United States Patent [19]

Grinna

[11] Patent Number: 5,439,807
[45] Date of Patent: Aug. 8, 1995

[54] METHODS FOR THE PREPARATION OF ENDOTOXIN-BINDING PROTEINS

[75] Inventor: Lynn S. Grinna, Middleburg, Va.

[73] Assignee: Xoma Corporation, Berkeley, Calif.

[21] Appl. No.: 72,063

[22] Filed: May 19, 1993

Related U.S. Application Data

[63] Continuation-in-part of Ser. No. 885,501, May 19, 1992, abandoned.

[51] Int. Cl.⁶ ............... C07K 1/22; C12N 15/12
[52] U.S. Cl. .................... 435/69.1; 435/69.7; 435/240.2; 435/240.23; 435/240.243; 435/244; 530/412; 530/416
[58] Field of Search ............ 435/69.1, 240.2, 252.3, 435/252.33, 320.1, 69.7; 530/350, 351, 412, 416, 387.1; 536/23.1, 23.4, 23.5, 23.53

[56] References Cited

U.S. PATENT DOCUMENTS 5,198,541  3/1993  Elsbach et al. .................... 435/69.1

FOREIGN PATENT DOCUMENTS 8905157  6/1989  WIPO .................... A61K 35/14

OTHER PUBLICATIONS

Gray et al. (1989), JBC vol. 264, pp. 9505–9509.
Schumann et al. (Sep. 1990), Science, vol. 249, pp. 1429–1431.
Ooi et al. (1987) JBC vol. 262, pp. 14891–14894.
Ion Exchange Chromatography, Principles and Methods p. 18, Pharmacia Fine Chemicals, 1983.

Primary Examiner—Garnette D. Draper
Assistant Examiner—John D. Ulm
Attorney, Agent, or Firm—Marshall, O'Toole, Gerstein, Murray & Borun

[57] ABSTRACT

Disclosed are improvements in methods for the isolation of endotoxin-binding proteins which are secreted by transfected host cells in appropriate cell culture media. In its preferred embodiment, the invention comprises addition of a cation exchange material to the media as the means of increasing the yield of recombinant endotoxin-binding proteins, such as bactericidal/permeability-increasing protein and lipopolysaccharide-binding protein.

6 Claims, 5 Drawing Sheets

COOMASSIE

WESTERN

COOMASSIE

WESTERN

5,439,807

METHODS FOR THE PREPARATION OF ENDOTOXIN-BINDING PROTEINS

This application is a continuation-in-part of U.S. patent application Ser. No. 07/885,501, filed May 19, 1992, now abandoned.

FIELD OF THE INVENTION

The present invention generally relates to improved procedures for the preparation of endotoxin-binding proteins by recombinant methods and more particularly to processes for the large scale production of recombinant endotoxin-binding proteins, such as bactericidal/permeability-increasing (BPI) protein, lipopolysaccharide-binding protein (LBP), high density lipoprotein, Limulus anti-LPS factor, tachyplesin, and structurally related proteins using genetically transformed host cells grown in culture, including culture in fermentors.

BACKGROUND OF THE INVENTION

Endotoxin, or lipopolysaccharide, is a component of the cell wall of Gram-negative bacteria and is implicated in the manifestation of acute bacterial infections. Numerous proteins have been reported which bind to the principal form of endotoxin, lipopolysaccharide ("LPS"). Examples of such LPS-binding proteins are bactericidal/permeability-increasing protein ("BPI protein") lipopolysaccharide-binding protein ("LBP"), incorporated by reference herein], high density lipoprotein, and tachyplesin [Nakamura, et al., *J. Biol. Chem.*, 263:16709–16713 (1988), incorporated by reference herein].

Certain of these proteins share significant structural homology. For example, both BPI and LBP possess a positively-charged amino terminal region of approximately 25 kDa which is the portion of each molecule which binds to the lipid A portion of LPS. See Schumann, et al., *Science*, 249:1429–1431 (1990).

Binding of BPI protein to membrane-bound LPS increases the envelope permeability of susceptible Gram negative bacteria. Ooi, et al., *J. Biol. Chem.*, 262:14891 (1987). BPI protein also binds to soluble LPS and human BPI protein has been isolated from polymorphonuclear neutrophils ("PMNs") by acid extraction combined with either ion exchange chromatography or E. coli affinity chromatography. Elsbach, et al. *J. Biol. Chem.*, 254:11000 (1979); Weiss et al., *Blood*, 69:652 (1987). The holo-BPI protein isolated from human PMNs has potent bactericidal activity against a broad spectrum of Gram-negative bacteria. Elsbach, et al., *J. Biol. Chem.*, 254:11000 (1979). This antibacterial activity appears to be associated with the amino terminal region of the isolated human holo-BPI protein. In contrast, the carboxyl terminal region of the isolated human BPI protein displays only slightly detectable anti-bacterial activity. Ooi, et al., *J. Exp. Med.*, 174:649 (1991).

Human DNA encoding BPI has been cloned and the amino acid sequence of the encoded protein has been elucidated [See, Gray et al., *J. Biol. Chem.*, 264:9505 (1989), hereinafter referred to as "Gray"; U.S. Letters Pat. No. 5,198,541, both of which are incorporated by reference herein] allowing for the large scale production of recombinant BPI and biologically active (e.g., amino and carboxyl terminal) fragments thereof. Initial attempts to purify recombinant BPI and BPI-related proteins from the medium of transfected cells utilizing traditional protein purification methods provided low yields. Pulse-chase experiments using $^{35}S$ labelled methionine and performed on cell cultures of transfected Chinese Hamster Ovary (CHO) cells expressing a recombinant product comprising the amino terminal 199 amino acids of the mature BPI protein [hereinafter rBPI(1-199)] indicated that the recombinant BPI fragment disappeared from the media during 3.5 hours to 7 hours of chase. Preliminary experimental procedures aimed at determining the basis for this low product yield indicated that the protein product displays significant "stickiness" and, in fact, adheres to itself, to other media components (including host cells), and to plastic and glass culture vessels. However, the precise reason(s) for protein loss have yet to be elucidated.

Like BPI protein, LBP binds to the lipid A portion of LPS. The holo-LBP protein is a 60 kD protein secreted by the liver and has been reported to be responsible for delivering LPS to macrophages. Ooi, et al., *J. Exp. Med.*, 174:649–65 (1991). Unlike BPI protein, LBP generally enhances the inflammatory response generated by LPS. For example, LBP stimulates LPS-induced tumor necrosis factor ("TNF") production.

Of interest to the present invention is the use of ion exchange materials in the isolation and purification of proteins and related substances. For example, published PCT application No. WO 89/05157 by Prior, et al., reports the purification and isolation of recombinant immunoglobulins by passing the cell culture medium over a chromatography column, wherein the immunoglobulin is adsorbed onto an exchange material. The immunogiobulin is then eluted by raising the salt concentration in the column. As another example, published PCT application No. WO 90/08159 by Robins, et al., reports removal of DNA from protein preparations by incubation in the presence of an anion exchange material. Wang, *Ann. N.Y. Acad. Sci.*, 413:313–321 (1983) presents the results of "hybrid" fermentation-extraction procedures for the production and isolation of a model antibiotic, cycloheximide, from fermentation cultures using non-ionic resins and noted that for one resin (XAD-4, Rohm and Haas, Philadelphia, Pa.) the product was absorbed on the resin surface making it "conceivable" to harvest the product from the resin.

Due to the utility of endotoxin binding proteins such as BPI protein and LBP as regulators of bacterial infection and the sequelae thereof, there exists a need in the art for improved methods for the isolation of such proteins from cell culture media.

BRIEF SUMMARY OF THE INVENTION

The present invention provides improved methods which facilitate the isolation of endotoxin-binding proteins, and especially lipid A binding proteins, in high yields.

The improved methods generally comprise the incorporation of a particulate cation exchange material into cell culture medium containing host cells which have been genetically transfected with DNA encoding the endotoxin-binding protein. Such proteins which are secreted into the cell culture medium by said host cells are reversibly bound to said cation exchange material. The cation exchange material with bound protein is then separated from the cell culture medium. Finally, the desired endotoxin-binding protein is then isolated from the cation exchange material.

The improved methods comprise the incorporation of a particulate cation exchange material (preferably S-Sepharose particles) into a cell culture medium containing host cells (preferably CHO-K1 or CHO-DG44 cells) which have been genetically transformed with DNA for expression of endotoxin-binding proteins or fragments thereof. The protein secreted into the cell medium by said host cells is reversibly bound to said cation exchange material. The cation exchange material with bound protein is then separated from the cell culture medium. Finally, the protein is isolated from the cation exchange material.

A presently preferred cation exchange material for practice of the invention is S-Sepharose and presently preferred isolation procedures comprise sequentially contacting the cation exchange material with a gradient or steps of increasing ionic strength.

In a preferred embodiment of the invention, the improved methods are applied to the production of recombinant BPI products, including but not limited to, bactericidal/permeability-increasing protein and biologically active fragments thereof as well as BPI-related products such as fusion proteins comprising, at their amino terminal, the BPI protein or a biologically active fragment thereof and, at their carboxy terminal, at least one constant domain of an immunoglobulin heavy chain region or an allelic variant thereof. Proteins of interest are secreted by genetically transformed host cells which are grown and maintained in a culture medium suitable for growth of host cells and secretion of the protein products.

Also, in another embodiment of the invention, the present improved methods are applied to the isolation of lipopolysaccharide-binding protein and amino-terminal fragments thereof.

The foregoing brief summary illustrates the preferred embodiments of the invention. Numerous aspects and advantages of the present invention will become apparent to the skilled artisan upon reading the following detailed description thereof.

DETAILED DESCRIPTION OF THE INVENTION

Figure 1A:
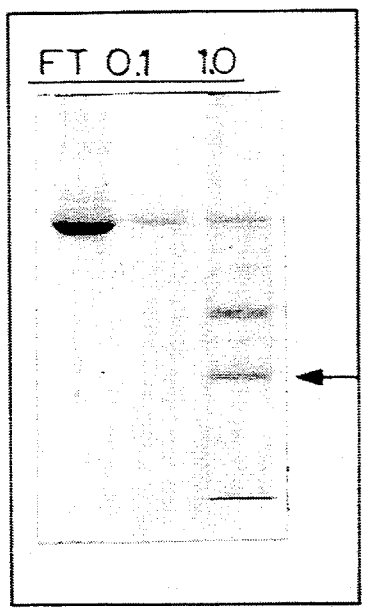
FIG. 1 depicts the results of comparative experiments using methods according to the invention and traditional chromatography methods to isolate the rBPI(-1–199) protein.

The following detailed description illustrates practice of methods of the invention in the context of recombinant production of three particular endotoxin-binding proteins, an amino-terminal portion of recombinant BPI protein ("rBPI protein"), an amino-terminal portion of recombinant LBP ("rLBP"), and rBPI-immunoglobulin fusion proteins ("rBPI-Ig fusions") from animal cell cultures. While the practice of the invention is exemplified herein by certain specific endotoxin-binding proteins, it is apparent to the skilled artisan that, due to their general structural and functional similarities, any endotoxin-binding protein may be isolated using methods of the invention. Such proteins include, but are not limited to, polymyxin B, high density lipoprotein, Limulus anti-LPS factor, and tachyplesin.

More specifically, Example 1 demonstrates that addition of the cation exchange material, S-Sepharose, to a cell culture medium results in increased yields of rBPI protein. Example 2 provides further results which demonstrate that introduction of the cation exchange material to cell cultures produces increased yields of rBPI protein. Example 3 illustrates practice of the improved methods in the isolation of rBPI-immunoglobulin fusion proteins and Example 4 demonstrates the use of a cation exchange material in the isolation of LBP.

EXAMPLE 1

Isolation of recombinant BPI products

Methods of the present invention were used to isolate a recombinant BPI protein which is the expression product of DNA encoding the 31-residue signal sequence and the first 199 amino acids of the N-terminus of the mature human BPI, as set out in SEQ ID NOS: 1 and 2 and is designated "rBPI(1-199)" herein. The DNA sequence employed differs from the BPI-encoding DNA sequence reported in Gray, et al., supra, in that the valine at position 151 of the rBPI(1-199) expression product is specified by GTG rather than by GTC as in Gray et al. and rBPI(1-199) encodes glutamic acid (specified by GAG) at position 185 rather than lysine (specified by AAG) as reported at that position in Gray et al. Recombinant production of rBPI(-1-199) protein is reported in Gazzano-Santoro, et al., *Infection and Immunity*, 60: 4754-4761 (1992), wherein the protein is referred to as "rBPI-23".

The host cells employed in this example were CHO-K1 cells transformed with a DNA vector including DNA encoding the initial 199 amino terminal amino acids of human BPI preceded by its endogenous 31 residue secretory signal sequence. The desired expression product, rBPI(1-199), was a biologically active fragment of the human BPI protein comprising the initial 199 amino terminal residues from which the signal sequence residues were removed in the course of post-translational secretory processing by the host cells.

Two roller bottles containing the transfected CHO host cells in Hams' F12 medium supplemented with 5% fetal bovine serum were prepared and the cells were grown to confluence (approximately 3 days). Once confluency was reached, the Hams F12 medium was removed and replaced with 500 ml of HB-CHO serum free medium (Irvine Scientific, Irvine, Calif.). In the first roller bottle, approximately 8 gm (wet weight) of sterilized S-Sepharose (Pharmacia, fast flow, #17-0511-01, Uppsula, Sweden) was added to one of the roller bottles for 3 days. The S-Sepharose was then isolated in order to generate a first column. Growth medium and S-Sepharose resin were removed from roller bottles, pooled and left for at least 15 minutes to allow the S-Sepharose to settle to the bottom of the container. The bulk of the medium, clear of resin, was removed by decanting and then filtered through a device, such as a fritted disc, to permit the removal of cells and the retention of the S-Sepharose. Following the decanting of the medium, the S-Sepharose was suspended in an Acetate buffer comprising 20 mM sodium acetate/acetic acid at pH 4.0 containing 0.1 M NaCl, stirred gently, and allowed to settle for 10 minutes. The buffer was then decanted and the S-Sepharose was transferred in a small volume to an appropriately-sized liquid chromatography column (1×10 cm, Econocolumn, BioRad, Richmond, Calif.).

The second roller bottle contained cells grown under the conditions stated above but in the absence of S-Sepharose. The medium from this second roller bottle was removed from the roller bottle. CHO cells were removed by centrifugation and the clarified medium was adjusted to contain 20 mM sodium acetate/acetic acid, pH 4.0. The medium was diluted to a conductivity of 10–15 mS/cm and was then loaded onto a second, traditional S-Sepharose column which had been equilibrated in 20 mM sodium acetate/acetic acid pH 4.0 (Acetate buffer) containing 0.1 M NaCl in order to maximize binding of the rBPI(1-199) protein.

Both the first and the second S-Sepharose columns were washed with 0.1 M NaCl-Acetate buffer until the A280 absorbance of the eluate was equal to that of the 0.1 M NaCl-Acetate buffer alone. The protein bound to each column was then eluted in a single step with 1.0 M NaCl-Acetate buffer.

The eluates from both columns were subjected to an ELISA assay wherein samples from the eluates were bound to Immulon-2 flat bottom multiwell plates (Dynetech Labs) in the presence of PBS overnight at 4° C. The plates were then washed with 0.05% Tween-20 in PBS, and then incubated with a 1:1000 dilution of rabbit anti-rBPI(1-199) antisera in PBS containing 0.05% Tween-20 for one hour at room temperature. After incubation, the plate was again washed with 0.05% Tween-20 in PBS and the ELISA was developed using the TMB reagent (Pierce Rockford, Ill.) according to the manufactures instructions and read at 450 nm in an EL309 microplate reader (Biotek Instruments, Winooski Vt.).

The ELISA results revealed that the eluate from the S-Sepharose column derived from the cell culture medium produced 3-8 fold stronger reactivity compared to the eluate from the S-Sepharose column to which medium had been added.

Example 2 provides further results, demonstrating that culturing S-Sepharose together with transfected CHO cells increased the yield of rBPI(1-199) protein produced by the transfected cells.

EXAMPLE 2

Quantitative Analysis of Isolation or rBPI(1-199)

In order to more quantitatively demonstrate that the yield of the rBPI(1-199) protein product obtained from the CHO cell cultures in Example 1 was greater when a cation exchange material was added to the cell culture medium, stained gel and Western analyses were carried out on the eluate samples described above.

Protein samples obtained from the 1.0 M NaCl-Acetate buffer eluates described in Example 1 were separated by SDS-polyacrylamide gel electrophoresis (SDS-PAGE). The samples of rBPI(1-199) were first adjusted to contain less than 0.5 M NaCl and were then precipitated by the addition of ice-cold acetone to a final concentration of 75%. The resulting protein precipitate was then pelleted by centrifugation at greater than 10,000 rpm for 5 to 10 minutes. The supernatant was removed and the precipitate was suspended in a gel sample buffer containing 8 M Urea, 2% SDS, 60 mM Tris HCl at pH 6.8. The suspended samples and appropriate protein molecular weight standards (BioRad, Richmond, Calif. and BRL, Bethesda, Md.) were heated to 95° C. for 3-5 minutes and then loaded onto uniform percentage or gradient percentage polyacrylamide gels (BioRad) and separated using a mini Protean II gel electrophoresis apparatus (BioRad). Following electrophoresis the gels were used directly for Coomassie staining (0.5% Coomassie Brilliant Blue-R, 25% isopropanol, 10% methanol, 10% acetic acid) or were used for electrotransfer. The proteins which were separated by SDS-PAGE were electrotransferred along with appropriate prestain standard protein (BioRad) onto either nitrocellulose (BA85, Schleicher and Schuell, Keene, N.H.) or PVDF (Immobilon-P, Millipore, Bedford, Mass.) membranes. The transfer was achieved in 10% CAPS (cyclohexylamino-1-propanesulfonic acid), 10% methanol, pH 11.5 for 20 minutes at 0.5 amps. The resulting blots were processed using a 1:1000 dilution of rabbit anti-human BPI (holoprotein) antisera and the Western Lite Chemiluminescent Detection System (Tropix System, Bedford, Mass.) according to the manufacturer's instructions. Gelatin (BioRad) at 0.25% was used in place of Tropix I-Block and the membranes were not dried following electrotransfer. The processed membranes were exposed to Cronex 4 film (Dupont, Wilmington, Del.).

The results of the stained gel and Western analysis are shown in FIG. 1, wherein quadrants A and B respectively present coomassie stain and Western blot analysis of the flow through (FT), 0.1M NaCl and 1.0 M NaCl eluates of columns formed from S-Sepharose beads incubated with culture medium. Quadrants C and D correspondingly present Coomassie stain and Western blot analysis of eluates from "traditional" columns of S-Sepharose. The arrow in quadrants A and C indicates the region corresponding the molecular weight of the rBPI(1-199) protein product. The yield of rBPI(1-199) protein was estimated to be at least 10-fold higher when the cationic exchange resin, S-Sepharose, had been added to the culture medium during cell growth.

Figure 2:
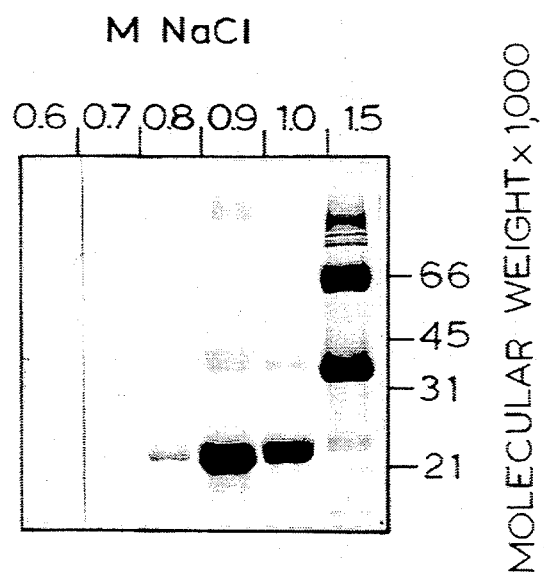
FIG. 2 depicts the results of the stepwise elution of rBPI(1-99) from S-Sepharose.
Figure 3:
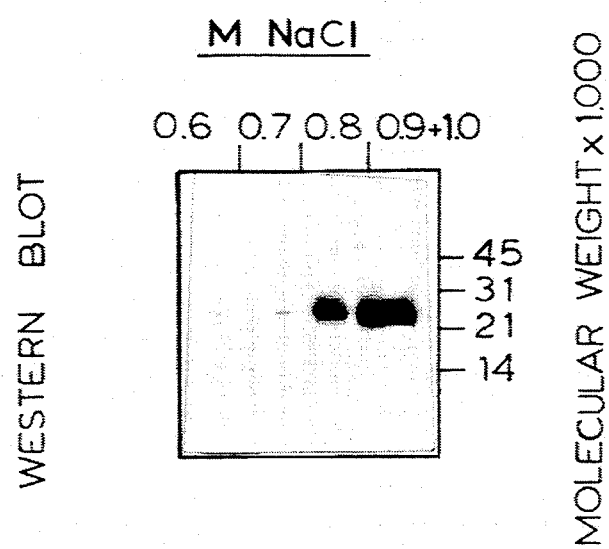
FIG. 3 depicts results of Western blot analysis of products prepared according to the invention.

Subsequent experiments involved the isolation of rBPI(1-199) from 20 to 40 g of S-Sepharose obtained from 3 to 5 roller bottles. The bound samples were eluted with increasing concentrations of NaCl in Acetate buffer. As shown in FIG. 2, the rBPI(1-199) product, visualized by Coomassie blue staining, is seen as a 23 kd protein in the 0.8, 0.9, 1.0, and 1.5 M NaCl-Acetate buffer eluates from the S-Sepharose columns. Little or no rBPI(1-199) protein was observed in the 0.2 M to 0.7 M NaCl-Acetate buffer eluates. The results of the Western Blot (FIG. 3) indicated that the strongest detectable rBPI(1-199) protein signal was obtained in the 0.8 M to 1.0 M NaCl-Acetate buffer eluates of the S-Sepharose columns.

The 1.5 M NaCl eluate from the S-Sepharose column also contained protein which was identified as rBPI(-1-199) (See FIG. 2, right lane). The 1.5 M NaCl-Acetate buffer eluate from the S-Sepharose column contained protein having molecular weights of approximately 40 kDa and greater than 66 kDa (FIG. 2) which, upon treatment with dithiothreitol, could be reduced to a single band of approximately 23 kDa. The reduced protein was cross-reactive with anti-BPI antisera and had the N-terminal sequence of correctly processed rBPI(1-199). The 40 kDa and greater than 66 kDa proteins appear to be disulfide-linked multimers of rBPI(-1-199).

The aforementioned results indicate that the addition of a cation exchange material to the cell culture medium improved recovery of rBPI(1-199) protein. In order to determine optimum concentration of S-Sepharose, 1.25 g to 10 g quantities of S-Sepharose were added to roller bottles containing 500 ml culture medium and transfected CHO cells and allowed to incubate as described above. The medium containing the cation exchange material was then poured into columns as described above. The columns were washed with 0.1M NaCl-Acetate buffer, then with 0.7 M NaCl-Acetate buffer and the rBPI(1-199) sample was eluted with 1.0 M NaCl-Acetate buffer. The yield of rBPI(1-199) was determined by chromatography on C4 reverse phase HPLC and was essentially constant for 2.5 g, 5.0 g, and 10 g quantities of S-Sepharose. The yield was decreased by approximately 50% in roller bottles containing only 1.25 g S-Sepharose per roller bottle.

Example 3 provides results demonstrating that increased yield of rBPI fusion proteins is obtained using methods according to the present invention.

EXAMPLE 3

Isolation of rBPI-I9 Fusion Proteins

Host cells employed in this example are CHO-DG44 cells transfected with a DNA vector comprising DNA encoding the initial 199 amino acids of BPI protein fused to at least one constant region of an immunoglobulin heavy chain. Construction of such "rBPI fusions" is provided in co-pending, co-owned U.S. patent application Ser. No. 07/885,911 now abandoned, as well as co-pending, co-owned, concurrently-filed continuation-in-part application Ser. No. 08/064,693, both of which are incorporated by reference herein. Transfected CHO-DG44 cells were grown in roller bottles. For each roller bottle, a T150 flask (containing 50 ml α-MEM without nucleosides and 10% dialyzed fetal bovine serum) was inoculated with transfected cells and the cells were grown to confluence (approximately 3-4 days). The cells were then trypsinized and transferred into a 900cm$^2$ roller bottle containing 500 ml Ham's F12 media and 10% fetal bovine serum and grown to confluence for approximately 3 days. Once confluency was reached, the Ham's F12 medium was removed and replaced with 500 ml HB-CHO serum-free medium (Irvine Scientific, Irvine, Calif.).

S-Sepharose beads, which had first been washed with Dulbecco's phosphate buffered saline (PBS) and autoclaved for 20 minutes at 120° C. were added aseptically to the roller bottles. The cells were then incubated at 37° C. for 3 days, at which time the beads and growth medium were removed and left undisturbed for at least 15 minutes. The bulk of the medium, clear of resin, was removed from by decanting and filtered through a device, such as a fritted disc, which allows removal of the cells and retention of the S-Sepharose. Following the decanting of the medium, the S-Sepharose was suspended in an acetate buffer comprising 20 mM sodium acetate/acetic acid, 0.1 M NaCl at pH 4.0, stirred gently, and allowed to settle for 10 minutes. The buffer was then decanted and the S-Sepharose was transferred in a small volume to an appropriately-sized liquid chromatography column. An Econocolumn (2.5×10 cm, BioRad, Richmond, Calif.) was used for a 20 to 40 g pooled sample of S-Sepharose collected from 3 to 5 roller bottles. The packed S-Sepharose column was washed with 0.1 M NaCl-acetate buffer until the A280 absorbance of the eluate was equal to that of the 0.1 M NaCl-acetate buffer alone, with 0.5 M NaCl-acetate buffer, with 1.0 M NaCl-acetate buffer and again with 1.5 M NaCl-acetate buffer.

Figure 4:
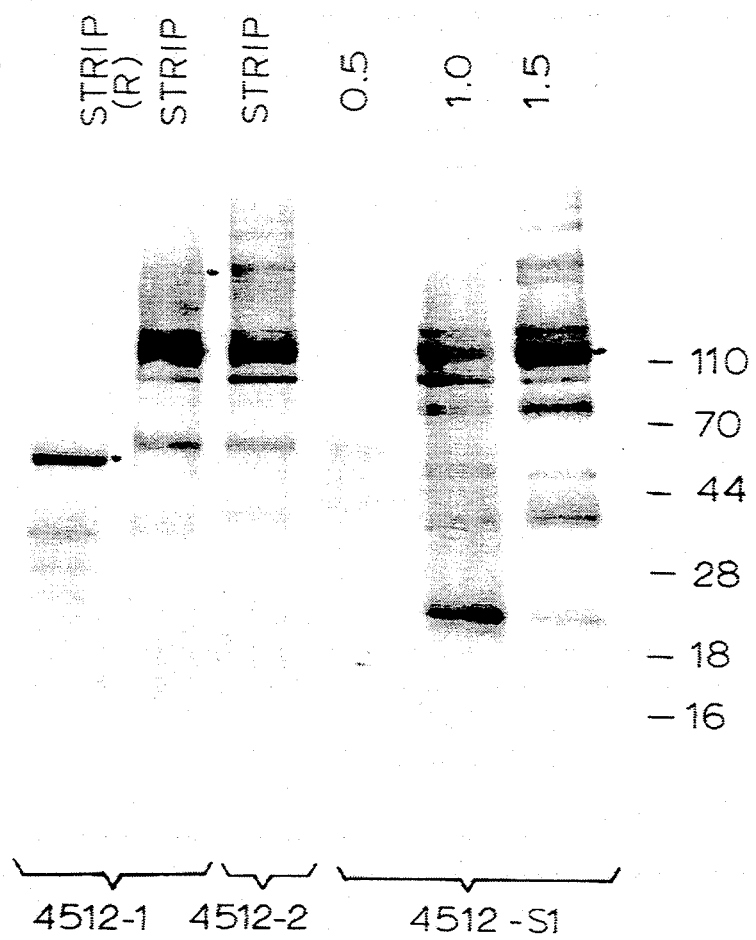
FIG. 4 is a Western blot depicting rBPI-Ig fusion products prepared according to the methods of the present invention.

Additional CHO-DG44 cells were prepared as above except that S-Sepharose beads were not added to the culture medium. Instead, an attempt was made to purify the rBPI fusion expression product utilizing two different protein A columns. A first sample of HB-CHO medium (see above) was filtered through a 0.45 μm filter in order to separate the CHO-DG44 cells from the rest of the medium. The sample was than adjusted to pH 8.0 and placed on a ProSepA (Bioprocessing) column. A second preparation was placed on an AvidGel (Bioprocessing) column. The elution of both columns was performed with 25 mM citrate buffer at pH 5.5. No rBPI fusion product was recovered from either protein A column. Nor was any product visualized from the ProSepA column following reduction (FIG. 4, lane 1). However, when the ProSepA and Avidgel columns were stripped with 100 mM citrate buffer at pH 3.0, rBPI fusion protein was detected as shown respectively in lanes 2 and 3 of FIG. 4. Lanes 4–6 of FIG. 4 represent the 0.5 M, 1.0 M, and 1.5 M eluates from the S-Sepharose column. Of the eluates from the S-Sepharose column, the 1.5 M eluate contained material corresponding to a fusion dimer of approximately 100 kD.

Example 4 provides results demonstrating that increased product yield of LBP is also obtained when cells transfected with DNA encoding LBP are incubated with a cation exchange resin.

EXAMPLE 4

Isolation Of Lipopolysaccharide-Binding Protein

The DNA sequence obtained for the 25 kD amino terminal of LBP is shown in SEQ ID NO: 3. That sequence differs in two regions from the reported sequence of Schumann, et al., Science, 249:1429–1431 (1990) (SEQ ID NO: 4). Those differences lead to amino acid differences at positions 129–132 and at position 149 (an asparagine residue at position 148 is encoded by GAT in Schumann, supra and by GAC in SEQ ID NO: 3). See also, published PCT Application 93/06228.

Host cells employed in this example are CHO-DG44 cells transfected with a DNA vector comprising DNA encoding the initial 197 amino acids of LBP, the expression product.

Transfected DG44 cells were grown in roller bottles. For each roller bottle, a T150 flask (containing 50 ml e-MEM without nucleosides and 10% dialyzed fetal bovine serum) was inoculated with transfected cells and the cells were grown to confluence (approximately 3-4 days). The cells were then trypsinized and transferred into a 900cm$^2$ roller bottle containing 500 ml Ham's F12 media and 10% fetal bovine serum and grown to confluence for approximately days. Once confluency was reached, the Ham's F12 medium was removed and replaced with 500 ml HB-CHO serum-free medium (Irvine Scientific, Irvine, Calif.).

S-Sepharose beads, which had first been washed with PBS and autoclaved for 20 minutes at 120 C were added aseptically to the roller bottles. The cells were then incubated at 37 C for 3 days, at which time the beads and growth medium were removed and left undisturbed for at least 15 minutes. The bulk of the medium, clear of resin, was removed from by decanting and filtered through a device, such as a fritted disc, which allows removal of the cells and retention of the S-Sepharose. Following the decanting of the medium, the S-Sepharose was suspended in an acetate buffer comprising 20 mM sodium acetate/acetic acid, 0.1 M NaCl at pH 4.0, stirred gently, and allowed to settle for 10 minutes. The buffer was then decanted and the S-Sepharose was transferred in a small volume to an appropriately-sized liquid chromatography column. An Econocolumn (2.5×10 cm, BioRad, Richmond, Calif.) was used for a 20 to 40 g pooled sample of S-Sepharose collected from 3 to 5 roller bottles. The packed S-Sepharose column was washed with 0.1 M NaCl-acetate buffer until the A280 absorbance of the eluate was equal to that of the 0.1 M NaCl-acetate buffer alone, with 0.7 M NaCl-acetate buffer and again with 1.0 M NaCl-acetate buffer.

Figure 5:
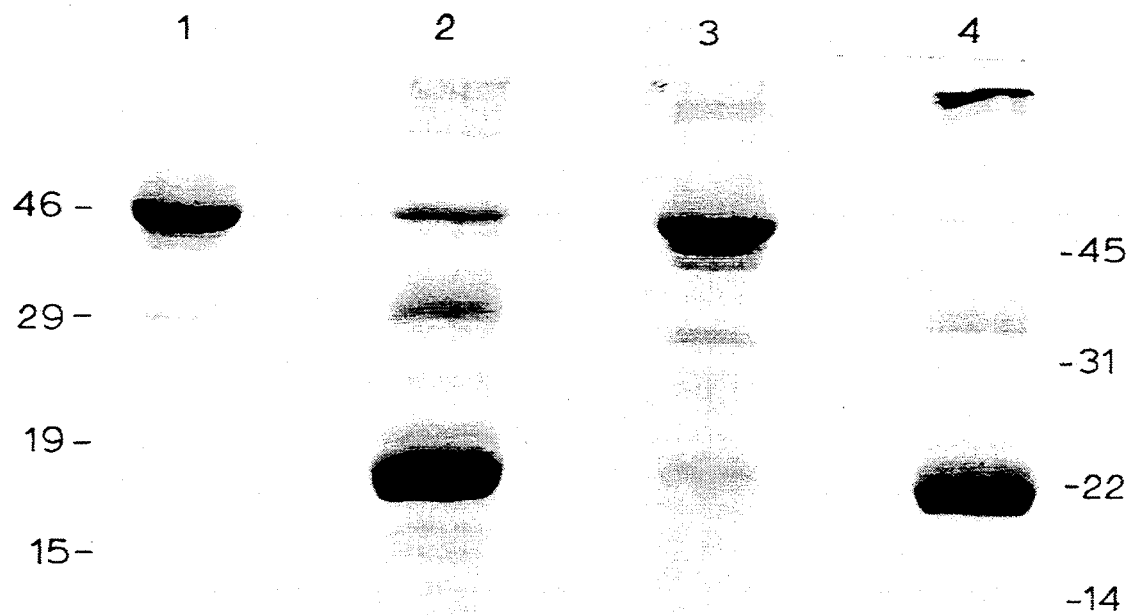
FIG. 5 depicts the results of a Coomassie-stained gel depicting isolation of LBP prepared according to methods of the present invention.

Yield of rLBP from cell cultures in which S-Sepharose beads were added is shown in FIG. 5 which is a Coomassie-stained gel of the 0.7 M (lanes 1 and 3) and 1.0 M (lanes 2 and 4) eluates described above. As shown in the figure, a significant amount of LBP eluted at 1.0 M. That S-Sepharose is able to facilitate LBP production from cell cultures is unexpected based on its calculated pI (6.6). In the culture medium used above, in which the pH was approximately 7.0, LBP would be expected, based on its pI, to be uncharged or slightly negatively charged and thus unreactive with a cation exchange resin, such as S-Sepharose.

Numerous modifications and variations in the practice of the invention are expected to occur to those skilled in the art upon consideration of the foregoing description of the presently preferred embodiments thereof. For example, the concentration of cation exchange material used in the invention may be varied according to the number and type (i.e., efficiency of production of the recombinant product) of cells used. As another example, while cation exchange materials other than S-Sepharose [e.g., Biorex 70, and SP (sulfopropyl) type materials such as SP-Sephadex as well as CM (carboxymethyl) type materials such as CM Sepharose and CM Sephadex] can be employed in processes of the invention, S-Sepharose was preferred as being most readily handled, subjected to sterilization processing, and the like. As still another example, while the above illustrative examples address recombinant production of endotoxin binding proteins in roller bottles, processes of the invention are readily "scaled up" to production in fermentors. Typical fermentation conditions for such processes as applied to production of rBPI(1–199) include use of a 600L working volume in a 750L Chemap (Woodbury, N.Y.) fermentor wherein CHO-K1 cells transfected with plasmid pING4502 [see, Gazzano et al., supra) are grown in ExCell 301 Medium (JRH Scientific) supplemented with 0.05% FBS and 0.01% Antifoam (U Carferm Adjuvant 27, Union Carbide) and 1% SP Sepharose "big beads" (100–300 micron diameter, Pharmacia) is added. Finally, the precise elution profiles of recombinant endotoxin-binding proteins isolated according to the invention are expected to vary depending on the precise identity of the protein involved. As one example, rBPI(1–199) is readily isolated from resin beads following a 0.7 M NaCl-Acetate buffer wash. However, yields of cysteine replacement analogs of BPI protein such as described in co-owned, co-pending U.S. patent application Ser. No. 08/013,801 by Theofan et al. are enhanced by isolation following a 0.6 M NaCl-Acetate buffer wash. Consequently, the only limitations which should be placed upon the scope of the present invention are those which appear in the appended claims.

---

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
      ( A ) LENGTH: 1813 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 31..1491

( i x ) FEATURE:
      ( A ) NAME/KEY: matpeptide
      ( B ) LOCATION: 124..1491

( x i ) SEQUENCE DESCRIPTION: SEQ ID NO:1:

```
CAGGCCTTGA GGTTTTGGCA GCTCTGGAGG ATG AGA GAG AAC ATG GCC AGG GGC         54
                                Met Arg Glu Asn Met Ala Arg Gly
                                -31 -30              -25

CCT TGC AAC GCG CCG AGA TGG GTG TCC CTG ATG GTG CTC GTC GCC ATA         102
Pro Cys Asn Ala Pro Arg Trp Val Ser Leu Met Val Leu Val Ala Ile
            -20             -15                     -10

GGC ACC GCC GTG ACA GCG GCC GTC AAC CCT GGC GTG GTG GTC AGG ATC         150
Gly Thr Ala Val Thr Ala Ala Val Asn Pro Gly Val Val Val Arg Ile
         -5                    1                5

TCC CAG AAG GGC CTG GAC TAC GCC AGC CAG CAG GGG ACG GCC GCT CTG         198
Ser Gln Lys Gly Leu Asp Tyr Ala Ser Gln Gln Gly Thr Ala Ala Leu
10              15                  20                  25
```

-continued

| | | | | | | | | | | | | | | | | |
|---|---|---|---|---|---|---|---|---|---|---|---|---|---|---|---|---|
| CAG | AAG | GAG | CTG | AAG | AGG | ATC | AAG | ATT | CCT | GAC | TAC | TCA | GAC | AGC | TTT | 246 |
| Gln | Lys | Glu | Leu | Lys | Arg | Ile | Lys | Ile | Pro | Asp | Tyr | Ser | Asp | Ser | Phe | |
| | | | | 30 | | | | 35 | | | | | | 40 | | |
| AAG | ATC | AAG | CAT | CTT | GGG | AAG | GGG | CAT | TAT | AGC | TTC | TAC | AGC | ATG | GAC | 294 |
| Lys | Ile | Lys | His | Leu | Gly | Lys | Gly | His | Tyr | Ser | Phe | Tyr | Ser | Met | Asp | |
| | | | 45 | | | | | 50 | | | | | 55 | | | |
| ATC | CGT | GAA | TTC | CAG | CTT | CCC | AGT | TCC | CAG | ATA | AGC | ATG | GTG | CCC | AAT | 342 |
| Ile | Arg | Glu | Phe | Gln | Leu | Pro | Ser | Ser | Gln | Ile | Ser | Met | Val | Pro | Asn | |
| | | 60 | | | | | 65 | | | | | 70 | | | | |
| GTG | GGC | CTT | AAG | TTC | TCC | ATC | AGC | AAC | GCC | AAT | ATC | AAG | ATC | AGC | GGG | 390 |
| Val | Gly | Leu | Lys | Phe | Ser | Ile | Ser | Asn | Ala | Asn | Ile | Lys | Ile | Ser | Gly | |
| | 75 | | | | | 80 | | | | | 85 | | | | | |
| AAA | TGG | AAG | GCA | CAA | AAG | AGA | TTC | TTA | AAA | ATG | AGC | GGC | AAT | TTT | GAC | 438 |
| Lys | Trp | Lys | Ala | Gln | Lys | Arg | Phe | Leu | Lys | Met | Ser | Gly | Asn | Phe | Asp | |
| 90 | | | | | 95 | | | | | 100 | | | | | 105 | |
| CTG | AGC | ATA | GAA | GGC | ATG | TCC | ATT | TCG | GCT | GAT | CTG | AAG | CTG | GGC | AGT | 486 |
| Leu | Ser | Ile | Glu | Gly | Met | Ser | Ile | Ser | Ala | Asp | Leu | Lys | Leu | Gly | Ser | |
| | | | | 110 | | | | | 115 | | | | | 120 | | |
| AAC | CCC | ACG | TCA | GGC | AAG | CCC | ACC | ATC | ACC | TGC | TCC | AGC | TGC | AGC | AGC | 534 |
| Asn | Pro | Thr | Ser | Gly | Lys | Pro | Thr | Ile | Thr | Cys | Ser | Ser | Cys | Ser | Ser | |
| | | | 125 | | | | | 130 | | | | | 135 | | | |
| CAC | ATC | AAC | AGT | GTC | CAC | GTG | CAC | ATC | TCA | AAG | AGC | AAA | GTC | GGG | TGG | 582 |
| His | Ile | Asn | Ser | Val | His | Val | His | Ile | Ser | Lys | Ser | Lys | Val | Gly | Trp | |
| | | 140 | | | | | 145 | | | | | 150 | | | | |
| CTG | ATC | CAA | CTC | TTC | CAC | AAA | AAA | ATT | GAG | TCT | GCG | CTT | CGA | AAC | AAG | 630 |
| Leu | Ile | Gln | Leu | Phe | His | Lys | Lys | Ile | Glu | Ser | Ala | Leu | Arg | Asn | Lys | |
| | 155 | | | | | 160 | | | | | 165 | | | | | |
| ATG | AAC | AGC | CAG | GTC | TGC | GAG | AAA | GTG | ACC | AAT | TCT | GTA | TCC | TCC | AAG | 678 |
| Met | Asn | Ser | Gln | Val | Cys | Glu | Lys | Val | Thr | Asn | Ser | Val | Ser | Ser | Lys | |
| 170 | | | | | 175 | | | | | 180 | | | | | 185 | |
| CTG | CAA | CCT | TAT | TTC | CAG | ACT | CTG | CCA | GTA | ATG | ACC | AAA | ATA | GAT | TCT | 726 |
| Leu | Gln | Pro | Tyr | Phe | Gln | Thr | Leu | Pro | Val | Met | Thr | Lys | Ile | Asp | Ser | |
| | | | | 190 | | | | | 195 | | | | | 200 | | |
| GTG | GCT | GGA | ATC | AAC | TAT | GGT | CTG | GTG | GCA | CCT | CCA | GCA | ACC | ACG | GCT | 774 |
| Val | Ala | Gly | Ile | Asn | Tyr | Gly | Leu | Val | Ala | Pro | Pro | Ala | Thr | Thr | Ala | |
| | | | 205 | | | | | 210 | | | | | 215 | | | |
| GAG | ACC | CTG | GAT | GTA | CAG | ATG | AAG | GGG | GAG | TTT | TAC | AGT | GAG | AAC | CAC | 822 |
| Glu | Thr | Leu | Asp | Val | Gln | Met | Lys | Gly | Glu | Phe | Tyr | Ser | Glu | Asn | His | |
| | | 220 | | | | | 225 | | | | | 230 | | | | |
| CAC | AAT | CCA | CCT | CCC | TTT | GCT | CCA | CCA | GTG | ATG | GAG | TTT | CCC | GCT | GCC | 870 |
| His | Asn | Pro | Pro | Pro | Phe | Ala | Pro | Pro | Val | Met | Glu | Phe | Pro | Ala | Ala | |
| | 235 | | | | | 240 | | | | | 245 | | | | | |
| CAT | GAC | CGC | ATG | GTA | TAC | CTG | GGC | CTC | TCA | GAC | TAC | TTC | TTC | AAC | ACA | 918 |
| His | Asp | Arg | Met | Val | Tyr | Leu | Gly | Leu | Ser | Asp | Tyr | Phe | Phe | Asn | Thr | |
| 250 | | | | | 255 | | | | | 260 | | | | | 265 | |
| GCC | GGG | CTT | GTA | TAC | CAA | GAG | GCT | GGG | GTC | TTG | AAG | ATG | ACC | CTT | AGA | 966 |
| Ala | Gly | Leu | Val | Tyr | Gln | Glu | Ala | Gly | Val | Leu | Lys | Met | Thr | Leu | Arg | |
| | | | | 270 | | | | | 275 | | | | | 280 | | |
| GAT | GAC | ATG | ATT | CCA | AAG | GAG | TCC | AAA | TTT | CGA | CTG | ACA | ACC | AAG | TTC | 1014 |
| Asp | Asp | Met | Ile | Pro | Lys | Glu | Ser | Lys | Phe | Arg | Leu | Thr | Thr | Lys | Phe | |
| | | | | 285 | | | | | 290 | | | | | 295 | | |
| TTT | GGA | ACC | TTC | CTA | CCT | GAG | GTG | GCC | AAG | AAG | TTT | CCC | AAC | ATG | AAG | 1062 |
| Phe | Gly | Thr | Phe | Leu | Pro | Glu | Val | Ala | Lys | Lys | Phe | Pro | Asn | Met | Lys | |
| | | 300 | | | | | 305 | | | | | 310 | | | | |
| ATA | CAG | ATC | CAT | GTC | TCA | GCC | TCC | ACC | CCG | CCA | CAC | CTG | TCT | GTG | CAG | 1110 |
| Ile | Gln | Ile | His | Val | Ser | Ala | Ser | Thr | Pro | Pro | His | Leu | Ser | Val | Gln | |
| | 315 | | | | | 320 | | | | | 325 | | | | | |
| CCC | ACC | GGC | CTT | ACC | TTC | TAC | CCT | GCC | GTG | GAT | GTC | CAG | GCC | TTT | GCC | 1158 |
| Pro | Thr | Gly | Leu | Thr | Phe | Tyr | Pro | Ala | Val | Asp | Val | Gln | Ala | Phe | Ala | |
| 330 | | | | | 335 | | | | | 340 | | | | | 345 | |
| GTC | CTC | CCC | AAC | TCC | TCC | CTG | GCT | TCC | CTC | TTC | CTG | ATT | GGC | ATG | CAC | 1206 |

|  |  |  |  |  |  |  |  |  |  |  |  |  |  |  |  |
|---|---|---|---|---|---|---|---|---|---|---|---|---|---|---|---|
| Val | Leu | Pro | Asn | Ser 350 | Ser | Leu | Ala | Ser 355 | Leu | Phe | Leu | Ile | Gly | Met 360 | His |

| ACA | ACT | GGT | TCC | ATG | GAG | GTC | AGC | GCC | GAG | TCC | AAC | AGG | CTT | GTT | GGA | 1254 |
|---|---|---|---|---|---|---|---|---|---|---|---|---|---|---|---|---|
| Thr | Thr | Gly | Ser 365 | Met | Glu | Val | Ser | Ala 370 | Glu | Ser | Asn | Arg | Leu 375 | Val | Gly | |

| GAG | CTC | AAG | CTG | GAT | AGG | CTC | CTC | CTG | GAA | CTG | AAG | CAC | TCA | AAT | ATT | 1302 |
|---|---|---|---|---|---|---|---|---|---|---|---|---|---|---|---|---|
| Glu | Leu | Lys 380 | Leu | Asp | Arg | Leu | Leu 385 | Leu | Glu | Leu | Lys | His 390 | Ser | Asn | Ile | |

| GGC | CCC | TTC | CCG | GTT | GAA | TTG | CTG | CAG | GAT | ATC | ATG | AAC | TAC | ATT | GTA | 1350 |
|---|---|---|---|---|---|---|---|---|---|---|---|---|---|---|---|---|
| Gly | Pro 395 | Phe | Pro | Val | Glu | Leu 400 | Leu | Gln | Asp | Ile | Met 405 | Asn | Tyr | Ile | Val | |

| CCC | ATT | CTT | GTG | CTG | CCC | AGG | GTT | AAC | GAG | AAA | CTA | CAG | AAA | GGC | TTC | 1398 |
|---|---|---|---|---|---|---|---|---|---|---|---|---|---|---|---|---|
| Pro 410 | Ile | Leu | Val | Leu | Pro 415 | Arg | Val | Asn | Glu | Lys 420 | Leu | Gln | Lys | Gly | Phe 425 | |

| CCT | CTC | CCG | ACG | CCG | GCC | AGA | GTC | CAG | CTC | TAC | AAC | GTA | GTG | CTT | CAG | 1446 |
|---|---|---|---|---|---|---|---|---|---|---|---|---|---|---|---|---|
| Pro | Leu | Pro | Thr 430 | Pro | Ala | Arg | Val | Gln 435 | Leu | Tyr | Asn | Val | Val 440 | Leu | Gln | |

| CCT | CAC | CAG | AAC | TTC | CTG | CTG | TTC | GGT | GCA | GAC | GTT | GTC | TAT | AAA | | 1491 |
|---|---|---|---|---|---|---|---|---|---|---|---|---|---|---|---|---|
| Pro | His | Gln | Asn 445 | Phe | Leu | Leu | Phe | Gly 450 | Ala | Asp | Val | Val | Tyr 455 | Lys | | |

| TGAAGGCACC | AGGGGTGCCG | GGGGCTGTCA | GCCGCACCTG | TTCCTGATGG | GCTGTGGGGC | 1551 |
|---|---|---|---|---|---|---|
| ACCGGCTGCC | TTTCCCCAGG | GAATCCTCTC | CAGATCTTAA | CCAAGAGCCC | CTTGCAAACT | 1611 |
| TCTTCGACTC | AGATTCAGAA | ATGATCTAAA | CACGAGGAAA | CATTATTCAT | TGGAAAAGTG | 1671 |
| CATGGTGTGT | ATTTTAGGGA | TTATGAGCTT | CTTTCAAGGG | CTAAGGCTGC | AGAGATATTT | 1731 |
| CCTCCAGGAA | TCGTGTTTCA | ATTGTAACCA | AGAAATTTCC | ATTTGTGCTT | CATGAAAAAA | 1791 |
| AACTTCTGGT | TTTTTCATG | TG | | | | 1813 |

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met -31 | Arg -30 | Glu | Asn | Met | Ala | Arg -25 | Gly | Pro | Cys | Asn | Ala -20 | Pro | Arg | Trp | Val |
|---|---|---|---|---|---|---|---|---|---|---|---|---|---|---|---|
| Ser -15 | Leu | Met | Val | Leu -10 | Val | Ala | Ile | Gly | Thr -5 | Ala | Val | Thr | Ala | Ala | Val 1 |
| Asn | Pro | Gly | Val 5 | Val | Val | Arg | Ile | Ser 10 | Gln | Lys | Gly | Leu | Asp 15 | Tyr | Ala |
| Ser | Gln | Gln 20 | Gly | Thr | Ala | Ala | Leu 25 | Gln | Lys | Glu | Leu | Lys 30 | Arg | Ile | Lys |
| Ile | Pro 35 | Asp | Tyr | Ser | Asp 40 | Ser | Phe | Lys | Ile | Lys 45 | His | Leu | Gly | Lys | Gly |
| His 50 | Tyr | Ser | Phe | Tyr | Ser 55 | Met | Asp | Ile | Arg | Glu 60 | Phe | Gln | Leu | Pro | Ser 65 |
| Ser | Gln | Ile | Ser | Met 70 | Val | Pro | Asn | Val | Gly 75 | Leu | Lys | Phe | Ser | Ile 80 | Ser |
| Asn | Ala | Asn | Ile 85 | Lys | Ile | Ser | Gly | Lys 90 | Trp | Lys | Ala | Gln | Lys 95 | Arg | Phe |
| Leu | Lys | Met | Ser 100 | Gly | Asn | Phe | Asp | Leu 105 | Ser | Ile | Glu | Gly | Met 110 | Ser | Ile |
| Ser | Ala | Asp 115 | Leu | Lys | Leu | Gly | Ser 120 | Asn | Pro | Thr | Ser | Gly 125 | Lys | Pro | Thr |
| Ile | Thr | Cys | Ser | Ser | Cys | Ser | Ser | His | Ile | Asn | Ser | Val | His | Val | His |

|     |     |     |     |     |     |     |     |     |     |     |     |     |     |     |     |
| --- | --- | --- | --- | --- | --- | --- | --- | --- | --- | --- | --- | --- | --- | --- | --- |
| 130 |     |     |     |     | 135 |     |     |     |     | 140 |     |     |     |     | 145 |
| Ile | Ser | Lys | Ser | Lys | Val | Gly | Trp | Leu | Ile | Gln | Leu | Phe | His | Lys | Lys |
|     |     |     |     | 150 |     |     |     |     | 155 |     |     |     |     | 160 |     |
| Ile | Glu | Ser | Ala | Leu | Arg | Asn | Lys | Met | Asn | Ser | Gln | Val | Cys | Glu | Lys |
|     |     |     |     | 165 |     |     |     |     | 170 |     |     |     |     | 175 |     |
| Val | Thr | Asn | Ser | Val | Ser | Ser | Lys | Leu | Gln | Pro | Tyr | Phe | Gln | Thr | Leu |
|     |     |     | 180 |     |     |     |     |     | 185 |     |     |     |     | 190 |     |
| Pro | Val | Met | Thr | Lys | Ile | Asp | Ser | Val | Ala | Gly | Ile | Asn | Tyr | Gly | Leu |
|     | 195 |     |     |     |     |     | 200 |     |     |     |     | 205 |     |     |     |
| Val | Ala | Pro | Pro | Ala | Thr | Thr | Ala | Glu | Thr | Leu | Asp | Val | Gln | Met | Lys |
| 210 |     |     |     |     | 215 |     |     |     |     | 220 |     |     |     |     | 225 |
| Gly | Glu | Phe | Tyr | Ser | Glu | Asn | His | His | Asn | Pro | Pro | Pro | Phe | Ala | Pro |
|     |     |     |     | 230 |     |     |     |     | 235 |     |     |     |     | 240 |     |
| Pro | Val | Met | Glu | Phe | Pro | Ala | Ala | His | Asp | Arg | Met | Val | Tyr | Leu | Gly |
|     |     |     |     | 245 |     |     |     |     | 250 |     |     |     |     | 255 |     |
| Leu | Ser | Asp | Tyr | Phe | Phe | Asn | Thr | Ala | Gly | Leu | Val | Tyr | Gln | Glu | Ala |
|     |     |     | 260 |     |     |     |     |     | 265 |     |     |     |     | 270 |     |
| Gly | Val | Leu | Lys | Met | Thr | Leu | Arg | Asp | Asp | Met | Ile | Pro | Lys | Glu | Ser |
|     |     | 275 |     |     |     |     | 280 |     |     |     |     | 285 |     |     |     |
| Lys | Phe | Arg | Leu | Thr | Thr | Lys | Phe | Phe | Gly | Thr | Phe | Leu | Pro | Glu | Val |
| 290 |     |     |     |     | 295 |     |     |     |     | 300 |     |     |     |     | 305 |
| Ala | Lys | Lys | Phe | Pro | Asn | Met | Lys | Ile | Gln | Ile | His | Val | Ser | Ala | Ser |
|     |     |     |     | 310 |     |     |     |     | 315 |     |     |     |     | 320 |     |
| Thr | Pro | Pro | His | Leu | Ser | Val | Gln | Pro | Thr | Gly | Leu | Thr | Phe | Tyr | Pro |
|     |     |     |     | 325 |     |     |     |     | 330 |     |     |     |     | 335 |     |
| Ala | Val | Asp | Val | Gln | Ala | Phe | Ala | Val | Leu | Pro | Asn | Ser | Ser | Leu | Ala |
|     |     |     | 340 |     |     |     |     | 345 |     |     |     |     | 350 |     |     |
| Ser | Leu | Phe | Leu | Ile | Gly | Met | His | Thr | Thr | Gly | Ser | Met | Glu | Val | Ser |
|     |     | 355 |     |     |     |     | 360 |     |     |     |     | 365 |     |     |     |
| Ala | Glu | Ser | Asn | Arg | Leu | Val | Gly | Glu | Leu | Lys | Leu | Asp | Arg | Leu | Leu |
| 370 |     |     |     |     | 375 |     |     |     |     | 380 |     |     |     |     | 385 |
| Leu | Glu | Leu | Lys | His | Ser | Asn | Ile | Gly | Pro | Phe | Pro | Val | Glu | Leu | Leu |
|     |     |     |     | 390 |     |     |     |     | 395 |     |     |     |     | 400 |     |
| Gln | Asp | Ile | Met | Asn | Tyr | Ile | Val | Pro | Ile | Leu | Val | Leu | Pro | Arg | Val |
|     |     |     | 405 |     |     |     |     | 410 |     |     |     |     | 415 |     |     |
| Asn | Glu | Lys | Leu | Gln | Lys | Gly | Phe | Pro | Leu | Pro | Thr | Pro | Ala | Arg | Val |
|     |     |     | 420 |     |     |     |     | 425 |     |     |     |     | 430 |     |     |
| Gln | Leu | Tyr | Asn | Val | Val | Leu | Gln | Pro | His | Gln | Asn | Phe | Leu | Leu | Phe |
|     |     | 435 |     |     |     |     | 440 |     |     |     |     | 445 |     |     |     |
| Gly | Ala | Asp | Val | Val | Tyr | Lys |     |     |     |     |     |     |     |     |     |
| 450 |     |     |     |     | 455 |     |     |     |     |     |     |     |     |     |     |

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CGTATGGCCA GCACCTGAAC TCCT      24

( 2 ) INFORMATION FOR SEQ ID NO:4:

( i ) SEQUENCE CHARACTERISTICS:
        ( A ) LENGTH: 17 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

GAGGGCTTTG TTGGAGA                                            17

(2) INFORMATION FOR SEQ ID NO:5:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

Pro Ala Pro Glu Leu Leu
1               5

(2) INFORMATION FOR SEQ ID NO:6:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

CAGTTTAAAA CTCACACATG CCCACC                                  26

(2) INFORMATION FOR SEQ ID NO:7:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

Lys Thr His Thr Cys Pro Pro Cys
1               5

(2) INFORMATION FOR SEQ ID NO:8:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

AGCTTCCCAG TTCCCAG                                            17

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:9:

TATTTTGGTC ATTACTGGCA GAGT                                          24

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GCACCTGCTA CTGACCGC                                                 18

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GGTCAGTAGC AG                                                       12

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

AAGCTTGTCG ACCAGGCCTT GAGGT                                         25

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

CTGGAGGCGG TGATGGTG                                                 18

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CGAAACAAGA TGAACAGCCA GGTCTGCGAG                                    30

( 2 ) INFORMATION FOR SEQ ID NO:15:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:15:

CTCGCAGACC TGGCTGTTCA TCTTGTTT                28

( 2 ) INFORMATION FOR SEQ ID NO:16:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

GCCACCRCCA TGG                                13

( 2 ) INFORMATION FOR SEQ ID NO:17:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:17:

ACTGTCGACG CCACCATGGC CAGGGGC                 27

( 2 ) INFORMATION FOR SEQ ID NO:18:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:18:

CCGCGGCTCG AGCTATATTT TGGTCAT                 27

I claim

1. In a method for the production of a recombinant endotoxin-binding protein comprising bactericidal/-permeability increasing protein or an endotoxin-binding NH$_2$-terminal fragment of bactericidal/permeability increasing protein, wherein genetically transformed host cells are cultured in a medium suitable for cell growth and maintenance and wherein the endotoxin-binding protein is secreted into said medium, the improvement comprising the following steps in sequence:
  incorporating a particulate cation exchange material into said host cell containing culture medium;
  culturing said host cells with said cation exchange particulate material to allow endotoxin-binding proteins secreted by said host cells to reversibly bind to said cation exchange material;
  separating said cation exchange material having endotoxin-binding protein bound thereto from said host cell containing culture medium; and
  isolating said endotoxin-binding protein from said cation exchange material.

2. The improvement of claim 1, wherein said cation exchange material is S-Sepharose.

3. The improvement of claim 1 wherein said isolating step comprises sequentially contacting said cation exchange medium with steps or a gradient of increasing ionic strength.

4. In a method for the production of a recombinant endotoxin-binding protein comprising lipopolysaccharide binding protein or an endotoxin-binding NH$_2$-terminal fragment of lipopolysaccharide binding protein, wherein genetically transformed host cells are cultured in a medium suitable for cell growth and maintenance and wherein the endotoxin-binding protein is secreted into said medium, the improvement comprising the following steps in sequence:

incorporating a particulate cation exchange material into said host cell containing culture medium;

culturing said host cells with said cation exchange particulate material to allow endotoxin-binding proteins secreted by said host cells to reversibly bind to said cation exchange material;

separating said cation exchange material having endotoxin-binding protein bound thereto from said host cell containing culture medium; and isolating said endotoxin-binding protein from said cation exchange material.

5. The improvement of claim 4, wherein said cation exchange material is S-Sepharose.

6. The improvement of claim 4 wherein said isolating step comprises sequentially contacting said cation exchange medium with steps of a gradient of increasing ionic strength.

* * * * *

UNITED STATES PATENT AND TRADEMARK OFFICE
CERTIFICATE OF CORRECTION

PATENT NO.  : 5,439,807

DATED       : August 8, 1995

INVENTOR(S) : Lynn Grinna

It is certified that error appears in the above-identified patent and that said Letters Patent is hereby corrected as shown below:

Column 2, line 31, "immunogiobulin" should be --immunoglobulin--.

Column 3, line 40, "Fig. 1 depicts" should be --Figs. 1A, 1B, 1C and 1D depict--.

Column 3, line 45, "rBPI(1-99)" should be --rBPI(1-199)--.

Column 5, line 32, "the manufactures" should be --the manufacturer's--.

Figure 1B:
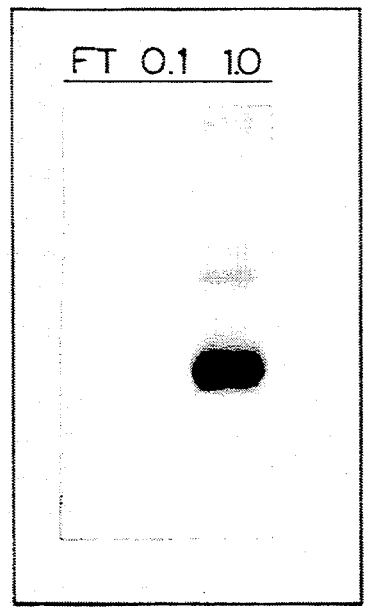

Column 6, line 24, "Fig. 1, wherein quadrants A and B" should be --Fig. 1A and Fig. 1B which--.

Figure 1C:
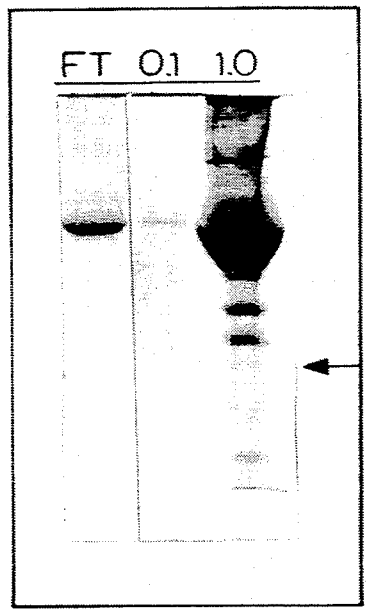
Figure 1D:
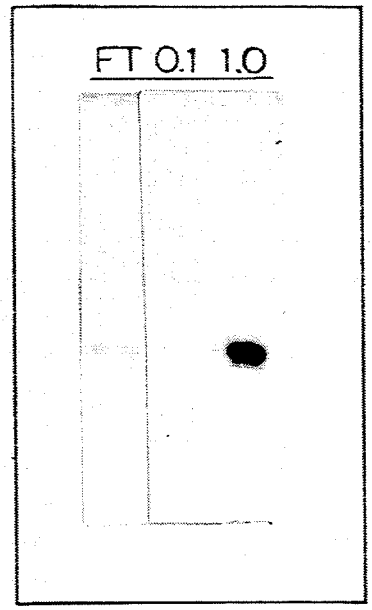

Column 6, line 28, "Quadrants C and D" should be --Fig. 1C and Fig. 1D--.

Column 6, line 31, "arrow in quadrants A and C indicates" should be --arrows in Fig. 1A and Fig. 1C indicate--.

Column 7, line 19, "of rBPI-I9" should be --of rBPI-Ig--.

Column 8, line 45, "e-MEM without" should be --α-MEM without--.

Column 8, line 51, "approximately days" should be --approximately 3 days--.

Column 10, line 13, "pING4502 [see," should be --pING4502 (see,--.

UNITED STATES PATENT AND TRADEMARK OFFICE
CERTIFICATE OF CORRECTION

PATENT NO. : 5,439,807

DATED : August 8, 1995

INVENTOR(S) : Lynn Grinna

It is certified that error appears in the above-identified patent and that said Letters Patent is hereby corrected as shown below:

In the sequence listing, at (iii) NUMBER OF SEQUENCES, "18" should be --4--.

In the sequence listing, SEQ ID NO:1, at the second occurrence of (ix) FEATURE: (A) NAME/KEY:, "matpeptide" should be --mat_peptide--.

In the sequence listing, SEQ ID NO:1, at position 151, "GTC" should be --GTG--.
  Val                                          Val In the sequence listing, SEQ ID NO:1, at position 185, "AAG" should be --GAG--.
  Glu                                          Lys In the sequence listing, SEQ ID NO:2, at position 185, "Lys" should be --Glu--.

In the sequence listing, replace SEQ ID NO.:3 and SEQ ID NO.:4 with substitute SEQ ID NO.: 3 and substitute SEQ ID NO.: 4 (paper and computer copy enclosed).

In the sequence listing, omit SEQ ID NO.:5 through SEQ ID NO. 18.

Signed and Sealed this

Eleventh Day of November, 1997

Attest:

BRUCE LEHMAN

Attesting Officer        Commissioner of Patents and Trademarks

SEQUENCE LISTING (1) GENERAL INFORMATION:

(i) APPLICANT: Grinna, Lynn (ii) TITLE OF INVENTION: Improved Methods for the Preparation of Endotoxin-Binding Proteins (iii) NUMBER OF SEQUENCES: 2

(iv) CORRESPONDENCE ADDRESS:
     (A) ADDRESSEE: Marshall, O'Toole, Gerstern, Murray & Borun
     (B) STREET: 6300 Sears Tower, 233 South Wacker Drive
     (C) CITY: Chicago
     (D) STATE: Illinois
     (E) COUNTRY: USA
     (F) ZIP: 60606-6402

(v) COMPUTER READABLE FORM:
     (A) MEDIUM TYPE: Floppy disk
     (B) COMPUTER: IBM PC compatible
     (C) OPERATING SYSTEM: PC-DOS/MS-DOS
     (D) SOFTWARE: PatentIn Release #1.0, Version #1.25

(vi) CURRENT APPLICATION DATA:
     (A) APPLICATION NUMBER:
     (B) FILING DATE:
     (C) CLASSIFICATION:

(vii) PRIOR APPLICATION DATA:
     (A) APPLICATION NUMBER: US 07/885,501
     (B) FILING DATE: 19-MAY-1992

(viii) ATTORNEY/AGENT INFORMATION:
     (A) NAME: Meyers, Thomas C.
     (B) REGISTRATION NUMBER: 36,989
     (C) REFERENCE/DOCKET NUMBER: 27129/31405

(ix) TELECOMMUNICATION INFORMATION:
     (A) TELEPHONE: 312/474-6300
     (B) TELEFAX: 312/474-0448
     (C) TELEX: 25-3856

(2) INFORMATION FOR SEQ ID NO:3:

(i) SEQUENCE CHARACTERISTICS:
     (A) LENGTH: 591 base pairs
     (B) TYPE: nucleic acid
     (C) STRANDEDNESS: single
     (D) TOPOLOGY: linear (ii) MOLECULE TYPE: cDNA (ix) FEATURE:
     (A) NAME/KEY: CDS
     (B) LOCATION: 1..591

(xi) SEQUENCE DESCRIPTION: SEQ ID NO:3:

```
GCC AAC CCC GGC TTG GTC GCC AGG ATC ACC GAC AAG GGA CTG CAG TAT      48
Ala Asn Pro Gly Leu Val Ala Arg Ile Thr Asp Lys Gly Leu Gln Tyr
 1               5                  10                  15
```

```
GCG GCC CAG GAG GGG CTA TTG GCT CTG CAG AGT GAG CTG CTC AGG ATC        96
Ala Ala Gln Glu Gly Leu Leu Ala Leu Gln Ser Glu Leu Leu Arg Ile
        20                      25                      30

ACG CTG CCT GAC TTC ACC GGG GAC TTG AGG ATC CCC CAC GTC GGC CGT       144
Thr Leu Pro Asp Phe Thr Gly Asp Leu Arg Ile Pro His Val Gly Arg
        35                      40                      45

GGG CGC TAT GAG TTC CAC AGC CTG AAC ATC CAC AGC TGT GAG CTG CTT       192
Gly Arg Tyr Glu Phe His Ser Leu Asn Ile His Ser Cys Glu Leu Leu
        50                      55                      60

CAC TCT GCG CTG AGG CCT GTC CCC GGC CAG GGC CTG AGT CTC AGC ATC       240
His Ser Ala Leu Arg Pro Val Pro Gly Gln Gly Leu Ser Leu Ser Ile
65                      70                      75                  80

TCC GAC TCC TCC ATC CGG GTC CAG GGC AGG TGG AAG GTG CGC AAG TCA       288
Ser Asp Ser Ser Ile Arg Val Gln Gly Arg Trp Lys Val Arg Lys Ser
                    85                      90                      95

TTC TTC AAA CTA CAG GGC TCC TTT GAT GTC AGT GTC AAG GGC ATC AGC       336
Phe Phe Lys Leu Gln Gly Ser Phe Asp Val Ser Val Lys Gly Ile Ser
            100                     105                     110

ATT TCG GTC AAC CTC CTG TTG GGC AGC GAG TCC TCC GGG AGG CCC ACA       384
Ile Ser Val Asn Leu Leu Leu Gly Ser Glu Ser Ser Gly Arg Pro Thr
        115                     120                     125

GTT ACT GCC TCC AGC TGC AGC AGT GAC ATC GCT GAC GTG GAG GTG GAC       432
Val Thr Ala Ser Ser Cys Ser Ser Asp Ile Ala Asp Val Glu Val Asp
        130                     135                     140

ATG TCG GGA GAC TTG GGG TGG CTC TTG AAC CTC TTC CAC AAC CAG ATT       480
Met Ser Gly Asp Leu Gly Trp Leu Leu Asn Leu Phe His Asn Gln Ile
145                     150                     155                 160

GAG TCC AAG TTC CAG AAA GTA CTG GAG AGC AGG ATT TGC GAA ATG ATC       528
Glu Ser Lys Phe Gln Lys Val Leu Glu Ser Arg Ile Cys Glu Met Ile
                165                     170                     175

CAG AAA TCA GTG TCC TCC GAT CTA CAG CCT TAT CTC CAA ACT CTG CCA       576
Gln Lys Ser Val Ser Ser Asp Leu Gln Pro Tyr Leu Gln Thr Leu Pro
            180                     185                     190

GTT ACA ACA GAG ATT                                                   591
Val Thr Thr Glu Ile
            195
```

(2) INFORMATION FOR SEQ ID NO:4:

(i) SEQUENCE CHARACTERISTICS:
        (A) LENGTH: 197 amino acids
        (B) TYPE: amino acid
        (D) TOPOLOGY: linear (ii) MOLECULE TYPE: protein (xi) SEQUENCE DESCRIPTION: SEQ ID NO:4:

```
Ala Asn Pro Gly Leu Val Ala Arg Ile Thr Asp Lys Gly Leu Gln Tyr
1               5                       10                      15

Ala Ala Gln Glu Gly Leu Leu Ala Leu Gln Ser Glu Leu Leu Arg Ile
            20                      25                      30

Thr Leu Pro Asp Phe Thr Gly Asp Leu Arg Ile Pro His Val Gly Arg
        35                      40                      45
```

```
Gly Arg Tyr Glu Phe His Ser Leu Asn Ile His Ser Cys Glu Leu Leu
 50                      55                  60
His Ser Ala Leu Arg Pro Val Pro Gly Gln Gly Leu Ser Leu Ser Ile
 65              70              75                          80
Ser Asp Ser Ser Ile Arg Val Gln Gly Arg Trp Lys Val Arg Lys Ser
                 85              90                  95
Phe Phe Lys Leu Gln Gly Ser Phe Asp Val Ser Val Lys Gly Ile Ser
            100             105             110
Ile Ser Val Asn Leu Leu Leu Gly Ser Glu Ser Ser Gly Arg Pro Thr
        115             120             125
Val Thr Ala Ser Ser Cys Ser Ser Asp Ile Ala Asp Val Glu Val Asp
    130             135             140
Met Ser Gly Asp Leu Gly Trp Leu Leu Asn Leu Phe His Asn Gln Ile
145             150             155                         160
Glu Ser Lys Phe Gln Lys Val Leu Glu Ser Arg Ile Cys Glu Met Ile
            165             170                 175
Gln Lys Ser Val Ser Ser Asp Leu Gln Pro Tyr Leu Gln Thr Leu Arg
            180             185             190
Val Thr Thr Glu Ile
            195
```